United States Patent [19]

McMahon et al.

[11] Patent Number: 5,738,086
[45] Date of Patent: Apr. 14, 1998

[54] METHOD OF INSTALLING AN ANTI-SIPHON FLOW RESTRICTER FOR A NEBULIZER

[75] Inventors: Michael David McMahon, Anaheim Hills; Andre Maurice Rustad, Etiwanda, both of Calif.

[73] Assignee: Baxter International Inc., Deerfield, Ill.

[21] Appl. No.: 439,390

[22] Filed: May 11, 1995

Related U.S. Application Data

[62] Division of Ser. No. 190,626, Feb. 2, 1994.

[51] Int. Cl.$^6$ .................. A61M 11/00; A61M 15/00; A62B 9/02; F16K 43/00
[52] U.S. Cl. .................. 128/200.21; 128/203.21; 128/205.24; 128/200.14; 137/315; 29/213.1; 285/3
[58] Field of Search .................. 137/315, 318; 251/89.5, 149; 29/432, 465, 798, 213.1, DIG. 33; 128/205.24, 201.28, 203.21, 203.11, 207.12, 207.16, 200.14, 200.21, 200.18; 138/37, 40, 44; 261/38, 52, 54–56, 61, 63, 64.1–64.6, 65; 264/154, 155, 267–271.1, DIG. 76; 403/2, 50; 285/3; 604/9, 10, 34, 87, 88, 148, 200, 201, 203, 205, 206, 237, 244, 335, 411, 415

[56] References Cited

U.S. PATENT DOCUMENTS

| | | | |
|---|---|---|---|
| Re. 33,642 | 7/1991 | Lester | 128/200.18 |
| Re. 33,717 | 10/1991 | Svoboda . | |
| 2,933,333 | 4/1960 | Bredtschneider et al. | 285/3 |
| 3,172,406 | 3/1965 | Bird et al. . | |
| 3,202,442 | 8/1965 | Abbey et al. | 285/3 |
| 3,572,590 | 3/1971 | Malone . | |
| 3,762,409 | 10/1973 | Lester . | |
| 3,838,686 | 10/1974 | Szekely . | |
| 3,844,585 | 10/1974 | Sands et al. | 285/3 |
| 4,048,997 | 9/1977 | Raghavachari et al. . | |
| 4,116,387 | 9/1978 | Kremer, Jr. et al. . | |
| 4,251,033 | 2/1981 | Rich et al. . | |
| 4,412,834 | 11/1983 | Kulin et al. | 604/29 |
| 4,456,179 | 6/1984 | Kremer . | |
| 4,462,397 | 7/1984 | Suzuki . | |
| 4,470,412 | 9/1984 | Nowacki et al. . | |
| 4,512,341 | 4/1985 | Lester . | |
| 4,566,452 | 1/1986 | Farr . | |
| 4,657,007 | 4/1987 | Carlin et al. . | |
| 4,746,067 | 5/1988 | Svoboda . | |
| 4,805,609 | 2/1989 | Roberts et al. . | |
| 4,852,561 | 8/1989 | Sperry . | |
| 4,941,468 | 7/1990 | Giovanni . | |
| 4,953,547 | 9/1990 | Poole, Jr. . | |
| 5,008,048 | 4/1991 | Ryder . | |
| 5,119,807 | 6/1992 | Roberts et al. | 128/200.24 |
| 5,235,969 | 8/1993 | Bellm . | |
| 5,277,175 | 1/1994 | Riggs et al. . | |
| 5,388,571 | 2/1995 | Roberts et al. | 128/203.12 |

FOREIGN PATENT DOCUMENTS

| | | |
|---|---|---|
| 1461679 | 11/1966 | France . |
| 1955 545 | 5/1971 | Germany . |
| 2019743 | 11/1979 | United Kingdom . |

*Primary Examiner*—Kimberly L. Asher
*Attorney, Agent, or Firm*—Thomas D. Bratschun; Francis Kowalik

[57] ABSTRACT

A method of installing an anti-siphon flow restricter into a gas flow lumen of a nebulizer includes providing an anti-siphon flow restricter having a side wall conforming to a cross section of the gas flow lumen, first and second ends at opposite ends of the side wall and an elastomeric diaphragm closing the first end of the side wall. The anti-siphon flow restricter is axially inserted into the gas flow lumen with the diaphragm leading. The diaphragm is slit and allowed to self-bias closed.

8 Claims, 3 Drawing Sheets

METHOD OF INSTALLING AN ANTI-SIPHON FLOW RESTRICTER FOR A NEBULIZER

This is a divisional of application Ser. No. 08/190,626 filed on Feb. 2, 1994, now pending.

BACKGROUND OF THE INVENTION

1. Technical Field

The present invention is directed toward nebulizers for medicating a patient's lungs and, more particularly, toward an improved disposable hand-held nebulizer.

2. Background Art

Nebulizers are devices for delivering atomized medication to air to be inhaled into the lungs of a patient. A variety of nebulizer structures are known in the medical field. An exemplary nebulizer is that disclosed in Farr, U.S. Pat. No. 4,566,452. Farr discloses a nebulizer having a nebulizer top and a reservoir bottom which are threadably connectable. A gas jet extends from the reservoir bottom along a longitudinal axis of the reservoir bottom. A liquid spray nozzle surrounds the gas jet defining a passageway for liquid between the gas jet and the liquid nozzle. At the top of the gas jet is a gas orifice which leads into a space in fluid communication with the spray nozzle passageway. A second orifice in a top of the spray nozzle is axially aligned with the orifice in the gas jet. A diffuser is connected to the nebulizer top and spaced from the nozzle orifice with the nebulizer top and reservoir bottom threadably connected. As gas is caused to flow through the gas jet, a vacuum is formed in the space between the gas orifice and the nozzle orifice, drawing fluid for nebulization to the fluid nozzle orifice. Nebulized fluid impinges upon the diffuser, causing oversized droplets to stick to the diffuser and providing a finely nebulized mist for delivery to the lungs of a patient.

One problem with nebulizers of the type discussed above can result during filling of the nebulizer reservoir. If a medical professional inadvertently fills the nebulizer reservoir sufficiently that the liquid orifice at the top of the fluid nozzle is covered with medication, medication may be siphoned into the gas jet and out of the reservoir. As a result, medication intended to be delivered to a patient may end up on a countertop as the nebulizer is being connected to an inhalation circuit. This can be a particularly significant problem with expensive medications costing as much as $100/cc or where time is of the essence in delivering the nebulized medication. The siphoning can also lead to build-up of medication in the gas lines, inhibiting proper operation of the nebulizer.

One attempt at solving the siphoning problem discussed above has been to provide a one-way check valve in the lumen of the gas jet. Lester, U.S. Pat. No. 3,762,409, discloses placing a one-way check valve in the gas jet lumen. However, one-way check valves known in the art have proven to be relatively expensive and relatively expensive to install in a gas jet lumen. This presents a significant impediment to providing such check valves, because hand-held nebulizers are molded, disposable assemblies which must be kept as inexpensive as possible to remain competitive in the market place. Furthermore, while the cost of the check valve and the cost of installing the check valve must be minimized, the check valve must never fail to permit gas to flow through the gas jet lumen. Should such failure occur, nebulization will be prevented, requiring disposal of the entire hand-held nebulizer assembly. Not only is the cost of the nebulizer wasted, at least residual amounts of potentially expensive medication is wasted. Such problems can result in considerable frustration to the medical professional using the nebulizer and irreparable damage to the goodwill of the nebulizer manufacturer. As a result of the cost and quality assurance problems, we know of no commercially available disposable hand-held nebulizer using an anti-siphon check valve in a gas jet lumen.

The present invention is directed toward overcoming one or more of the problems discussed above in a novel and simple manner.

SUMMARY OF THE INVENTION

One aspect of the present invention is a nebulizer including a housing having an aerosol outlet and a wall defining a reservoir for a liquid. A gas jet extends through the wall, the gas jet defining a gas flow lumen and having a gas orifice at its distal end within the reservoir. A gas inlet is connected to the gas jet. A liquid nozzle is spaced from the gas jet for nebulization of liquid conveyed by the liquid nozzle to the gas orifice. A diaphragm having a slit which is biased closed is maintained within the gas flow lumen, with the slit transverse to the length of the lumen.

The present invention further provides the gas flow lumen including a lesser diameter portion proximate the gas orifice and a greater diameter portion proximate the gas inlet with a shoulder therebetween. The diaphragm includes a side wall extending lengthwise of the lumen having a step integrally formed about the periphery of the side wall. The step is configured to cooperatively engage the shoulder for halting axial inserting of the diaphragm into the gas flow lumen. The diaphragm is preferably made of an elastomer.

Another aspect of the invention is an anti-siphon flow restricter for a nebulizer having a gas flow lumen. The anti-siphon flow restricter includes a cylindrical side wall having a first and a second end with a diaphragm closing the first end of the cylindrical side wall. The cylindrical side wall and the diaphragm are configured for axial insertion into the gas flow lumen, with the side wall engaging an inner wall of the gas flow lumen and the diaphragm transverse to the gas flow lumen. A slit within the diaphragm is biased closed by a biasing structure. The anti-siphon flow restricter is preferably integrally formed of a single piece of elastomeric material with the biasing structure being the elastomeric material.

The anti-siphon flow restricter including a slit diaphragm mounted within the gas flow lumen prevents siphoning of liquid medication through the gas jet lumen, thereby eliminating a potential avenue for loss of expensive liquid medication. The anti-siphon flow restricter is considerably less expensive than one-way check valves known in the art and can be installed quickly and inexpensively, thereby providing a significant advantage for the nebulizer structure within which it is used without a significant impact on the cost of the nebulizer.

Another aspect of the present invention is a method of installing an anti-siphon flow restricter into a gas flow lumen of a nebulizer. A nebulizer is provided, the nebulizer having a housing including an aerosol outlet and a wall defining a reservoir for a liquid. A gas jet extends through the wall, with a gas inlet connected to the gas jet having a lengthwise gas flow lumen. A liquid nozzle is mounted relative to the gas nozzle for nebulization of liquid sprayed from the liquid nozzle. Also provided is an anti-siphon flow restricter having a sidewall with first and second ends conforming to a cross-section of the gas flow lumen, a diaphragm closing the first end of the side wall. The anti-siphon flow restricter is axially inserted with the diaphragm leading into the gas flow lumen. During insertion of the anti-siphon flow restricter, the diaphragm is slit.

Preferably, an elongate diaphragm inserting tool having a blade at its leading end is provided with the inserting of the diaphragm and the slitting of the diaphragm being performed using the inserting tool. Preferably, the blade is axially extended from the leading end of the inserting tool during insertion of the diaphragm and upon completion of insertion of the diaphragm the blade is retracted into the leading end of the tool. Preferably, following slitting of the diaphragm, pressurized gas is introduced into the gas flow lumen and the pressurized gas is monitored to verify that the diaphragm has been slit.

The method of installing an anti-siphon flow restricter into a gas flow lumen of a nebulizer of the present invention provides for expedient and inexpensive installation of an anti-siphon flow restricter to a nebulizer flow lumen, so as to provide the many advantages discussed above. Furthermore, the method assures that as each anti-flow restricter is inserted into the gas flow lumen it is automatically split, addressing the critical quality assurance deficiencies of prior art check valves.

Another aspect of the present invention is a tool for installing a split diaphragm flow restricter including a diaphragm into a lumen or conduit. The tool includes an elongate rod having a cross-section which is receivable by axial insertion of a leading end of the rod into a lumen or conduit. A blade having a cutting surface is on the leading end of the rod. A structure at the leading end of the rod abuts the diaphragm without penetrating the diaphragm.

Preferably, a hollow is located proximate the leading end of the rod with an opening to the hollow at the leading end and the blade is telescopingly received in the hollow of the rod through the open leading end with the cutting surface corresponding to the open leading end. The tool further includes means biasing the blade with the cutting surface received within the open leading end of the hollow and means for axially extending the blade from the open leading end upon the open leading end encountering a force opposing forward axial movement of the rod. A channel runs lengthwise of the blade.

The tool for installing a slit diaphragm flow restricter in a lumen of a conduit facilitates expedient installation of a slit diaphragm flow restricter and further assures a user that the diaphragm will, in fact, be slit. The retractable blade minimizes the likelihood of workers being injured using the tool and protects the blade from damage.

DETAILED DESCRIPTION OF THE PREFERRED EMBODIMENT

Figure 1:
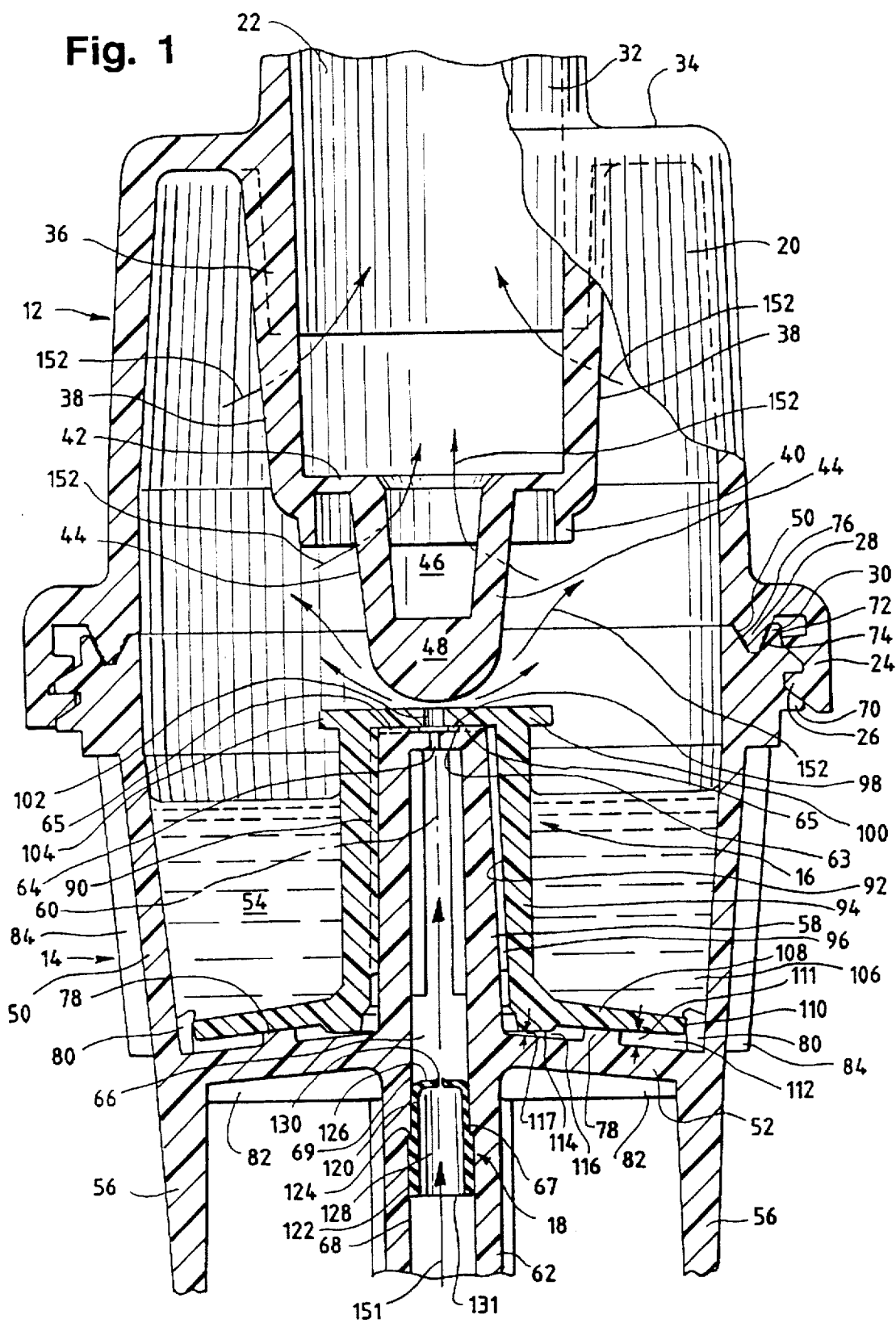
FIG. 1 is an elevation view of a nebulizer of the present invention shown in partial section.

A nebulizer (10) includes a nebulizer top (12), a reservoir bottom (14), a liquid spray nozzle (16) and an anti-siphon flow restricter (18).

The nebulizer top (12) has a side wall (20) defining at one end an aerosol outlet (22) and at an opposite end a collar (24) having female threads (26). An annular V-shaped protrusion (28) extends downward from the bottom side wall (20) of the nebulizer top (12) just inside the collar (24). The surface (30) of the V-shaped annular protrusion is textured or frosted. A cylindrical wall (32) having a diameter less than that of the side wall (20) extends upward from a shoulder (34) of the nebulizer top (12) around the outlet (22) and is connectable at a distal end to an inhalation tube of a patient ventilator (not shown) or other structures for conveying nebulized medication from the aerosol outlet to a patient's lungs. A first baffle (36) descends from the shoulder (34) inside the side wall (20) around the aerosol outlet (22). Three legs (38) (two shown in FIGS. 1 and 2) located 120° apart descend from the first baffle (36) and are joined to a second baffle (40). An annular flange (42) extends inwardly around the top of the second baffle (40) and a pair of diffuser legs (44) having longitudinal spaces (46) therebetween extend downward from the inwardly extending annular flange (42) to support a nebulizer diffuser (48).

Figure 2:
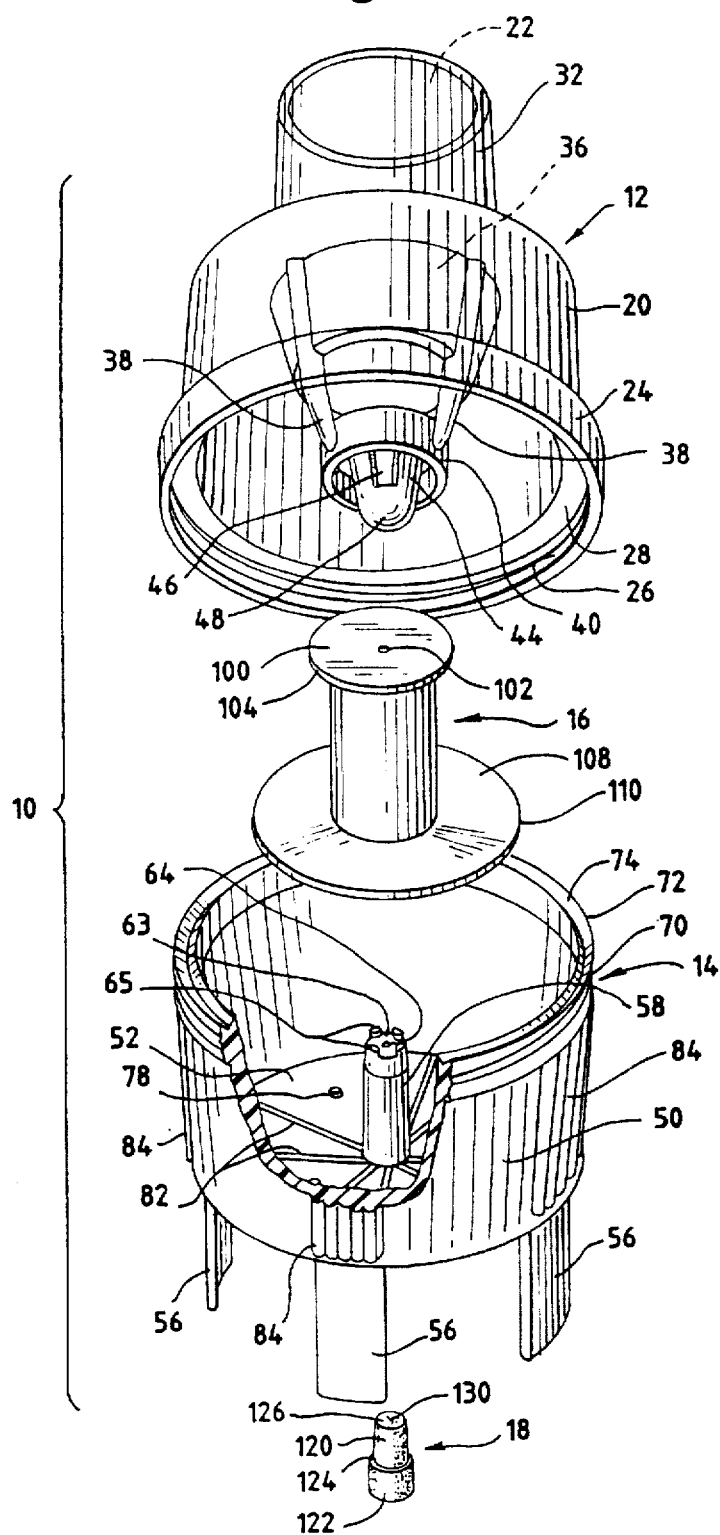
FIG. 2 is an exploded perspective view of the nebulizer of the present invention.

The reservoir bottom (14) has a peripheral side wall (50) extending upwardly and outwardly from a bottom wall (52) in essentially a frustoconical manner, the peripheral side wall (50) and the bottom wall (52) defining a liquid reservoir (54). Four legs (56) (three shown in FIG. 2) descend from the outside of the bottom wall (52) to support the nebulizer (10) in a vertical orientation, as illustrated in FIGS. 1 and 2. The bottom wall (52) extends inwardly and upwardly from the peripheral side wall (50) to an air jet (58), a feature which helps reduce the height of the reservoir bottom (14) and thus the overall height of the nebulizer (10). The air jet (58) extends through the center of the bottom wall (52) along a longitudinal axis (60) of the reservoir bottom (14). The bottom of the gas jet (58) is a gas inlet (62) connectable to a supply of gas through a flexible tube (neither of which is shown). At the top (63) of the gas jet (58) is a gas orifice (64) surrounded by circumferentially spaced axial spacers (65). A gas flow lumen (66) running through the gas jet (58) and gas inlet (62) has an annular step (67) between a greater diameter portion (68) and a lesser diameter portion (69) of the gas flow lumen (66).

Male threads (70) surround the top (72) of the side wall (50) and are configured to threadably engage the female threads (26) of the nebulizer top (12) as illustrated in FIG. 1. An annular V-shaped channel (74) is in the top (72) of the side wall (50) and is configured to nestingly receive the annular V-shaped protrusion (28) of the nebulizer top (12). As is the case with the annular V-shaped protrusion (28), the surface (76) of the annular V-shaped channel (74) is textured or frosted to facilitate a liquid seal between the annular V-shaped channel 74 and the nestingly received annular V-shaped protrusion (28).

A plurality of spacers (78) extend upwardly from the bottom wall (52) of the nebulizer bottom (14). Around the periphery of the bottom wall (52) are circumferentially spaced clips (80). A plurality of radiating ribs (82) extend from the bottom wall (52) between the gas jet (58) and the side wall (50) to reinforce the bottom wall (52). Undulating ridges (84) extend longitudinally at 90° intervals from the side wall (50) of the reservoir bottom (14).

The liquid spray nozzle (16) is configured to envelope the gas jet (58) as illustrated in FIG. 1 and is spaced from the gas jet (58) axially by the spacers (65) and radially by circumferentially spaced longitudinal spacers (90) extending inwardly from an inner surface (92) of a side wall (94) of the liquid spray nozzle (16). The longitudinal spacers (90)

define a nozzle liquid passageway (96) between the spray nozzle (16) and the gas jet (58). The nozzle liquid passageway (96) opens to a space (98) maintained between the top (63) of the gas jet (58) by the spacers (65). The top (100) of the liquid spray nozzle (16) has a fluid orifice (102) which is coaxial with the gas orifice (64) upon the spray nozzle (16) being secured in the reservoir bottom (14) in the manner discussed below. An outwardly projecting radial flange (104) surrounds the reservoir top (100) and provides a barrier against liquid (106) within the reservoir (54) overrunning the top (100) of the spray nozzle (16) when the nebulizer (10) is tilted from its vertical orientation.

A collector flange (108) extends around the bottom of the spray nozzle (16) in a parallel spaced relationship from the bottom wall (52) of the reservoir bottom (14). The peripheral edge (110) of the collector flange (108) is in close proximity to the side wall (50). The peripheral edge (110) is snapped into the reservoir bottom (14) and maintained therein by the circumferentially spaced clips (80) in the manner illustrated in FIG. 1. A space 111 between the collector flange (108) and the reservoir bottom wall (52) is maintained at a select distance by the spacers (78). The space (111) defines a collector flange passageway (112). The space (111) is preferably between 0.025 and 0.04 inches, with a space of 0.035 inches being preferred. At the bottom of the liquid nozzle (16) is a liquid seal collar (114). The liquid seal collar (114) extends downward into the collector flange passageway (112) to define a liquid seal space (116) having a gap (117) of not more than 0.02 inches. Preferably, the gap (117) of the liquid seal space is about 0.011 inches.

Figure 3:
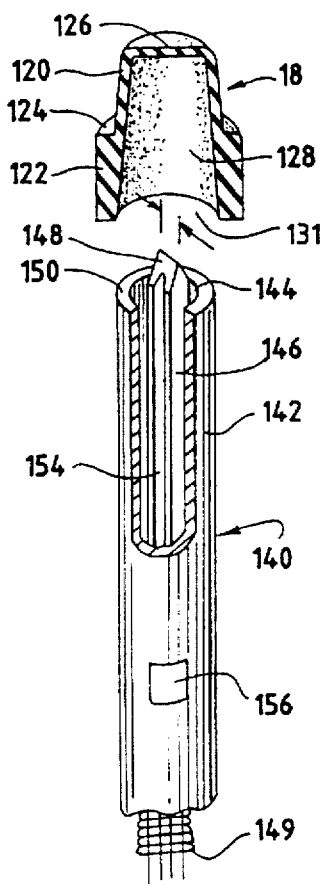
FIG. 3 is a perspective partial section view of a tool for installing a slit diaphragm flow restricter of the present invention including a perspective section view of an anti-siphon flow restricter of the present invention.
Figure 4:
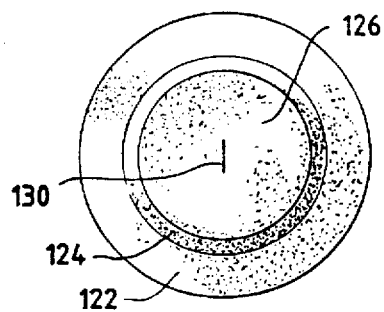
FIG. 4 is a plan view of the anti-siphon flow restricter of the present invention.

The anti-siphon flow restricter (18) has a lesser diameter side wall 120 and an axially spaced greater diameter side wall (122) joined by an annular shoulder (124). A planar diaphragm (126) extends across the end of the lesser diameter side wall (120) so as to define a cup-shaped interior (128) of the anti-siphon flow restricter (18)—see FIG. 1 and FIG. 3. A slit (130) is in the diaphragm (126) transverse to the length of the anti-siphon flow restricter (18). As best seen in FIG. 1, the anti-siphon flow restricter (118) is axially received within the gas lumen (66) of the gas jet (58), with the annular shoulder (124) of the anti-siphon flow restricter (18) in engagement with the annular step (67) within the gas jet lumen (66). As best seen in FIGS. 1, 3 and 4, the greater diameter side wall (122) is of increasing diameter between the annular shoulder (124) and the open end (131). This increasing diameter helps to axially secure the anti-siphon flow restricter (18) within the gas flow lumen.

FIG. 3 illustrates a tool (140) for installing the anti-siphon flow restricter (18) in the gas lumen (66). The tool (140) consists of a hollow rod or housing (142) having an open leading end (144) with a retractable blade (146) telescopingly received therein. The retractable blade (146) has a leading cutting edge (148) configured to provide the slit (130) in the anti-siphon flow restricter (18). A spring (149) housed within the rod (142) biases the retractable blade (146) inside the open leading end (144) of the rod (142). The periphery of the rod (142) is configured so that the rod (142) is axially receivable within the cup-shaped interior (128) of the anti-siphon flow restricter (18). The leading edge (150) abuts against the interior surface of the diaphragm (126) and applies an axial force against the diaphragm (126) without penetrating the diaphragm (126). The tool is configured so that as the leading edge (150) encounters a force opposing further axial insertion of the anti-siphon flow restricter (18), the retractable blade (146) telescopingly extends from the open leading end (144) and the cutting surface (148) cuts through the diaphragm (146) defining the slit (130). As the force on the leading edge subsides, the retractable blade (146) is retracted back into the rod (142) by the spring (149).

In operation, the aerosol outlet (22) is connected to an inhalation line of a ventilator which in mm is connected to a patient's mouthpiece. Compressed gas such as air represented by the arrow (151) is supplied through the gas inlet (62) during the inhalation cycle of a patient's breathing, while the compressed air is cut off during the exhalation cycle of the patient's breathing. Compressed air supplied through the air inlet (62) passes through the gas flow lumen (66) of the gas jet (58). As the compressed air impinges upon the diaphragm (126) the slit (130) is forced open and air passes out the gas orifice (64). As the air passes through the space (98) and out of the fluid orifice (102), it creates a vacuum or venturi effect in the space (98) which draws liquid from the liquid reservoir (54) through the collector flange liquid passageway (112) and the nozzle liquid passageway (96) into the air stream passing through the gas orifice (64). The liquid is nebulized as a result of entering the high velocity air stream and is further nebulized when it impinges upon the diffuser (48). The resulting aerosol represented by the arrows (152) then impinges upon the first and second baffles (36,40) causing larger droplets to coalesce and fall back into the reservoir (14), while droplets of the proper size remain suspended in the air and pass around the first and second baffles (36,40) and are discharged through the aerosol outlet (22) for inhalation by a patient.

During the exhalation cycle while the flow of compressed air is cut off from the gas jet, liquid medication has been known to be siphoned into the gas jet lumen (66). The anti-siphon flow restricter (18) prevents this liquid from flowing into the compressed air source. More particularly, when the flow of compressed air represented by the arrow is cut off, the elastomeric material comprising the diaphragm (126) causes the slit (130) to close. This serves the function of cutting off the negative pressure which could cause siphoning of liquid into the gas orifice (64) and further provides a barrier to any liquid which happens to enter the gas orifice (64). During the next inhalation cycle the compresses gas blows any liquid which may have collected on the top of the diaphragm (126) out of the gas jet, where it may then be nebulized and inhaled by a patient.

Figure 5:
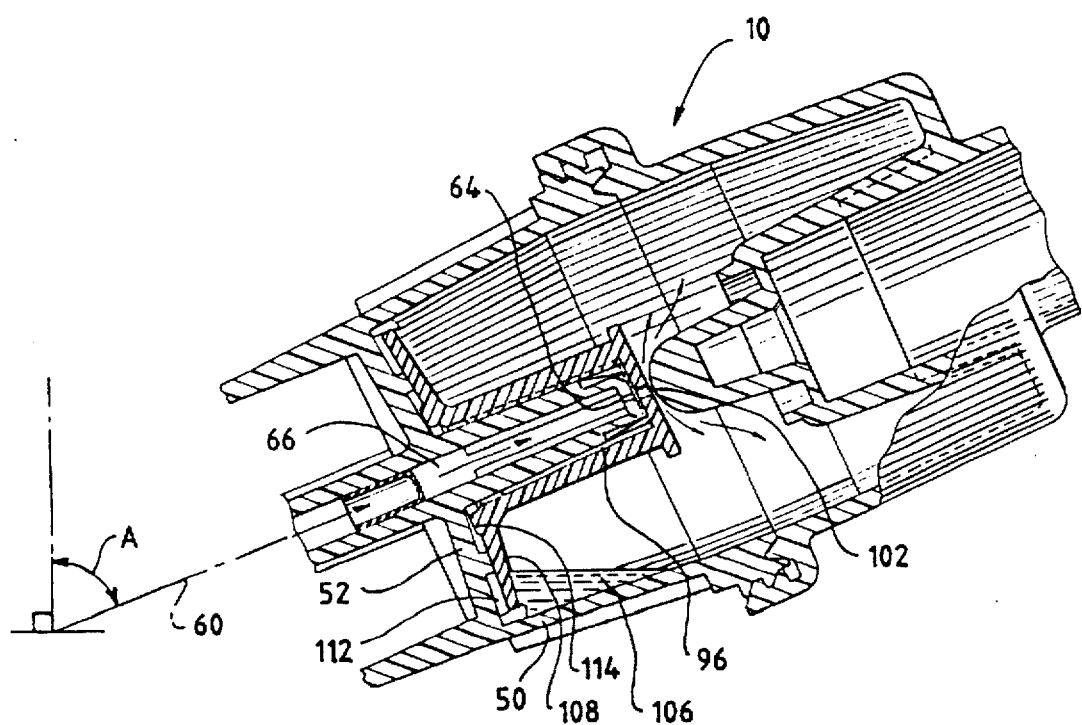
FIG. 5 shows the nebulizer of FIG. 1 inclined from its vertical orientation.

During use, the nebulizer (10) may be inadvertently disrupted from its vertical orientation by a patient. However, by cooperative interaction of the liquid seal collar (114) and the collector flange (108), liquid will continue to be delivered to the gas orifice for nebulization. More particularly, as illustrated in FIG. 5, the nebulizer can be inclined up to an angle A of 70° from vertical without interruption of liquid flow. This is accomplished by a liquid seal which forms in the liquid seal space (116). Fluid can still be dram through the collector flange passageway (112) by the venturi effect of the gas stream flowing from the gas orifice (64) through the liquid orifice (102). Virtually all the liquid within the reservoir will be drawn into the collector flange passageway (112) for nebulization and minimal amounts will adhere by fluid tension between the liquid seal collar (114) and the bottom wall (52) as the final drops of liquid are drawn into the nozzle liquid passageway (96) for nebulization. The liquid seal is maintained in the liquid seal space (116) by surface tension of the liquid and by virtue of liquid flowing through the collector flange passageway (112) and the nozzle liquid passageway (96).

The nebulizer (10) is assembled fitting the liquid spray nozzle (16) over the gas jet (58) and pressing down upon the top (100) to engage the clips (80) to the flange periphery (110). The nebulizer top (12) is then threadably engaged with the reservoir bottom (14) to form a nebulizer housing. With the nebulizer top (12) threadably engaged with the reservoir bottom (14), the nebulizer diffuser (48) is spaced a distance of about 0.022 inches from the fluid orifice (102) to ensure generation of an aerosol having correct particle size.

The anti-siphon flow restricter (18) is axially inserted through the bottom of the gas inlet (62) using the tool (140). More particularly, the anti-siphon flow restricter (18) having an unslit diaphragm (126) is placed over the open leading end (144) of the tool (140). The tool (140) with the anti-siphon flow restricter (118) thereon is then axially inserted into the bottom of the gas inlet (62). As friction between the side wall (120,122) of the anti-siphon flow restricter (118) and the interior of the flow lumen (66) opposes axial insertion of the anti-siphon flow restricter, the retractable blade (146) is caused to extend from the open leading end (144) of the tool (140). The cutting surface (148) cuts through the diaphragm (126) forming the slit (130). The tool (140) can be inserted into the gas flow lumen (66) until the annular shoulder (124) engages the annular step (67) of the gas flow lumen (66). At this point, further insertion of the anti-siphon flow restricter is prevented and, in the event it has not yet happened, the cutting edge (148) of the blade pierces the diaphragm (126). The tool (140) is then withdrawn from the gas inlet (62), causing retraction of the blade (146) into the open leading end (144) of the rod (142). In a highly preferred embodiment, a channel (154) is provided lengthwise of the blade (146). Compressed air can be fed through the channel (154) following retraction of the blade (146). A pressure sensor (156) measures for excessive pressure buildup in the channel (154) which would indicate that the slit (130) was not formed in the diaphragm. If such a pressure buildup occurs, the nebulizer can be identified and shipment of a defective nebulizer to a user is prevented.

The anti-siphon flow restricter inserted within a gas flow lumen prevents siphoning of liquid medication through the gas jet lumen, thereby eliminating a potential avenue for loss of expensive liquid medication. The slit diaphragm construction of the anti-siphon flow restricter is considerably less expensive than one-way check valves known in the art. Moreover, the anti-siphon flow restricter can be quickly and inexpensively installed in a flow lumen, thereby providing a significant advantage over other nebulizer structures without a significant impact on nebulizer cost. The method of installing the anti-siphon flow restricter and the tool for installing the anti-siphon flow restricter facilitate the expedient and inexpensive installation of the anti-siphon flow restricter. Furthermore, the method and tool ensures that each anti-siphon flow restricter inserted into the gas flow lumen is actually split, thereby eliminating quality assurance deficiencies of prior art check valves.

We claim:

1. A method of installing an anti-siphon flow restricter into a gas flow lumen of a nebulizer comprising the steps of:

a) providing a nebulizer having a housing having an aerosol outlet and a wall defining a reservoir for a liquid, a gas jet extending through the wall, a gas inlet connected to the gas jet having a lengthwise gas flow lumen, a liquid nozzle mounted relative to the gas nozzle for nebulization of liquid sprayed from the liquid nozzle and a liquid passageway extending between the reservoir and the liquid nozzle to provide a liquid flow therebetween;

b) providing an anti-siphon flow restricter having a side wall conforming to a cross-section of the gas flow lumen, first and second ends at opposite ends of the side wall and a planar elastomeric diaphragm closing the first end of the side wall;

c) axially inserting the anti-siphon flow restricter with the planar diaphragm leading into the gas flow lumen; and d) during or after step c), slitting the planar diaphragm; and e) allowing the planar diaphragm slit to self-bias closed.

2. The method of claim 1 wherein in step a) the gas flow lumen includes a lesser diameter portion proximate the gas jet and a greater diameter portion away from the gas jet and a step between lesser and greater diameter portions, and in step b) the side wall is cylindrical with a shoulder integrally formed about the periphery of the side wall and configured to cooperatively engage the step, the method further including the step of f) axially inserting the anti-siphon flow restricter into the gas inlet lumen until the shoulder engages the step.

3. The method of claim 2 wherein step d) is performed following the step f).

4. The method of claim 2 further comprising the steps of:

g) providing an elongate diaphragm inserting tool having an axially extending and retractable blade telescopingly nested in a leading end of the tool, step c) and f) being performed using the tool of step g); and h) during step c) and f) axially extending the blade form the leading end to effect step d).

5. The method of claim 4 further comprising the steps of:

i) withdrawing the diaphragm inserting tool of step g) from the gas flow lumen; and j) axially retracting the blade into the leading end of the tool.

6. The method of claim 1 further comprising the step of:

f) providing an elongate diaphragm inserting tool having a linear blade at a leading end of the tool, steps c) and d) being performed using the inserting tool of step f) with the leading end abutting the diaphragm.

7. The method of claim 6 further comprising the step of:

g) axially extending the blade from the leading end during step c) and upon completion of step c), axially retracting the blade into the leading end of the tool.

8. The method of claim 1 further comprising the steps of:

f) following step e), introducing pressurized gas into the gas flow lumen; and g) monitoring the introduction of pressurized gas to verify that step d) has been performed.

* * * * *